United States Patent [19]

Stabinger et al.

[11] Patent Number: 5,477,726
[45] Date of Patent: Dec. 26, 1995

[54] APPARATUS FOR DETERMINING THE DENSITY OF LIQUIDS AND GASES FROM A PERIOD OF AN OSCILLATOR FILLED WITH A TEST SAMPLE

[76] Inventors: Hans Stabinger, Peterstalstr, 156, A-8042 Graz; Hans Leopold, Sonnleitenweg 17, A-8043 Graz, both of Austria

[21] Appl. No.: 877,520

[22] Filed: May 1, 1992

[51] Int. Cl.⁶ .................................................. G01N 9/00
[52] U.S. Cl. ........................................................ 73/32 A
[58] Field of Search ................................ 73/32 A, 32 R, 73/24.05, 30.01

[56] References Cited

U.S. PATENT DOCUMENTS

| | | | |
|---|---|---|---|
| 3,339,400 | 9/1967 | Banks | 73/32 A |
| 3,385,104 | 5/1968 | Banks | 73/580 |
| 3,910,101 | 10/1975 | Kratky et al. | 73/32 A |
| 4,524,610 | 6/1985 | Fitzgerald et al. | 73/54.25 |
| 4,602,498 | 7/1986 | Glikberg et al. | 73/32 A |
| 4,838,084 | 6/1989 | Leopold | 73/32 A |
| 4,872,335 | 10/1989 | Tsuruoka | 73/32 A |
| 4,926,682 | 5/1990 | Holm-Kennedy et al. | 73/54.01 |
| 5,005,400 | 4/1991 | Lew | 73/32 A |
| 5,237,853 | 8/1993 | Cassaday et al. | 73/32 A |
| 5,253,533 | 10/1993 | Lam et al. | 73/861.37 |
| 5,339,258 | 8/1994 | Stabinger | 73/32 A |

FOREIGN PATENT DOCUMENTS

| | | |
|---|---|---|
| 356943 | 6/1980 | Austria . |
| 0222503 | 5/1987 | European Pat. Off. . |
| 2208525 | 6/1974 | France . |
| 1498548 | 7/1964 | Germany . |
| 331539 | 8/1976 | Germany . |
| 2001761 | 2/1979 | United Kingdom . |
| 2187286 | 9/1987 | United Kingdom . |
| 2236591 | 4/1991 | United Kingdom . |
| WO9012306 | 10/1990 | WIPO . |

OTHER PUBLICATIONS

Langdon, R. M., "Vibratory Process Control Transducers", The Marconi Review, vol. XLIII (1980), No. 218, Rugby, Great Britain, pp. 156–175.

*Primary Examiner*—Hezron E. Williams
*Assistant Examiner*—Christine K. Oda
*Attorney, Agent, or Firm*—Cushman, Darby & Cushman

[57] ABSTRACT

An apparatus for determining the density of liquids and gases from the length of a period of an oscillator filled with a test sample, an oscillation amplifier being provided for its excitation which excites the oscillator in its mechanical resonance frequency via one or a plurality of actuators and which emits a periodic electrical signal, the period of which corresponds with the period of the oscillator or a multiple thereof. To make highly accurate measurements possible it has been provided that the actuators are disposed between the installation site of the oscillator or the housing of the oscillator rigidly connected with the installation site, and a countermass. In an alternative embodiment, the oscillator housing is eliminated so that the actuator or actuators are interposed directly between the oscillator and the countermass. A thermostatically-controllable plate and thermostatically-controllable elements may be used as in the previous embodiment.

11 Claims, 1 Drawing Sheet

APPARATUS FOR DETERMINING THE DENSITY OF LIQUIDS AND GASES FROM A PERIOD OF AN OSCILLATOR FILLED WITH A TEST SAMPLE

BACKGROUND OF THE INVENTION

1. Field of the Invention

The invention relates to an apparatus for determining the density of liquids and gases from the length of a period of an oscillator filled with a test sample, an oscillation amplifier being provided for its excitation which excites the oscillator in its mechanical resonance frequency via electromechanical transducers and which emits a periodic electrical signal, the period of which corresponds with the period of the oscillator or a multiple thereof.

2. Description of the Related Art

Such an apparatus was disclosed, for example, in Austrian Letters Patent 356,943. In this known apparatus, transducers consisting of coils and permanent magnets are attached to the oscillator at locations with broad amplitudes. The oscillator is particularly sensitive in regard to density changes of the test sample at these locations. These locations are also particularly sensitive to temperature because of the thermal expansion coefficient of the test sample. The self-heating of a coil caused by its excitation current therefore is a source of errors in connection with highly accurate density measurements.

SUMMARY OF THE INVENTION

It is the object of the invention to improve the accuracy of the density measurements of an apparatus of the previously mentioned type. It is particularly intended to make the measurement insensitive to temperature. A further object of the invention consists of providing an apparatus of the previously mentioned type which prevents the self-heating of a coil caused by its excitation current as well as the associated heating of the sample undergoing the density measurement.

This is attained in accordance with the invention in an apparatus of the previously mentioned type in that one or more transducers are disposed between the installation site of the oscillator or the housing of the oscillator rigidly connected with the installation site, and a countermass.

The oscillator, which is preferably embodied in the shape of a letter U and which contains the sample to be tested, is disposed in a housing. The housing of the oscillator is supported on one or a plurality of actuators, which in turn are disposed on a countermass. The actuators transform electrical signals into mechanical oscillations and can be in the form of piezo-electrical elements, for example.

Driving of the actuator or actuators is performed by an oscillation amplifier, which in turn is controlled by means of a sensor disposed in the housing of the oscillator.

The oscillator is excited in its mechanical resonance frequency by the excitation of the oscillation amplifier via an actuator or actuators, in that the housing of the oscillator is being moved in relation to the countermass.

By means of this relative movement attainable through the invention, the direct disposition of the actuators on the oscillator required for this is avoided in an advantageous and simple manner, and the undesirable heat flow from the actuator to the oscillator is therefore avoided. In addition, the countermass is also a good heat sink for the dissipated power.

Thus, it is assured by means of these steps of the invention that the thermal effect on the sample contained in the oscillator is reduced to a large extent, which increases the accuracy of the measurement.

To reduce the thermal effect further, it can be provided in accordance with a further characteristic of the invention that means for thermal insulation are disposed between the actuators and the oscillator or its housing.

These means for thermal insulation can be, for example, a thermostatically-controllable plate, such as a cooling plate, which has the purpose of being an additional heat sink between the actuators and the housing of the oscillator.

This results in the advantage that no heat, which could have an effect on the measurement results, is transferred from the dissipated power of the actuators to the oscillator.

A heat flow from the actuators to the oscillator is practically prevented in this way.

In a further development of the invention, it can be provided for additional thermal insulation that the oscillator or its housing is supported on the thermostatically-controllable plate via thermostatically-controllable elements, for example, Peltier elements.

The structural step of the thermostatically-controllable plate is optional. A variant of the invention can also consist in that the actuators are on the one side disposed on the countermass and, on the other, on the oscillator or its housing, with thermostatically-controllable elements, such as Peltier elements, interposed.

With this variant of the invention there is also the advantage that a very high degree of temperature stability of the sample is assured. A further improved thermal insulation between the actuators and the oscillator is assured by exactly these thermostatically-controllable elements.

DETAILED DESCRIPTION OF THE PRESENTLY PREFERRED EXEMPLARY EMBODIMENTS

Figure 1:
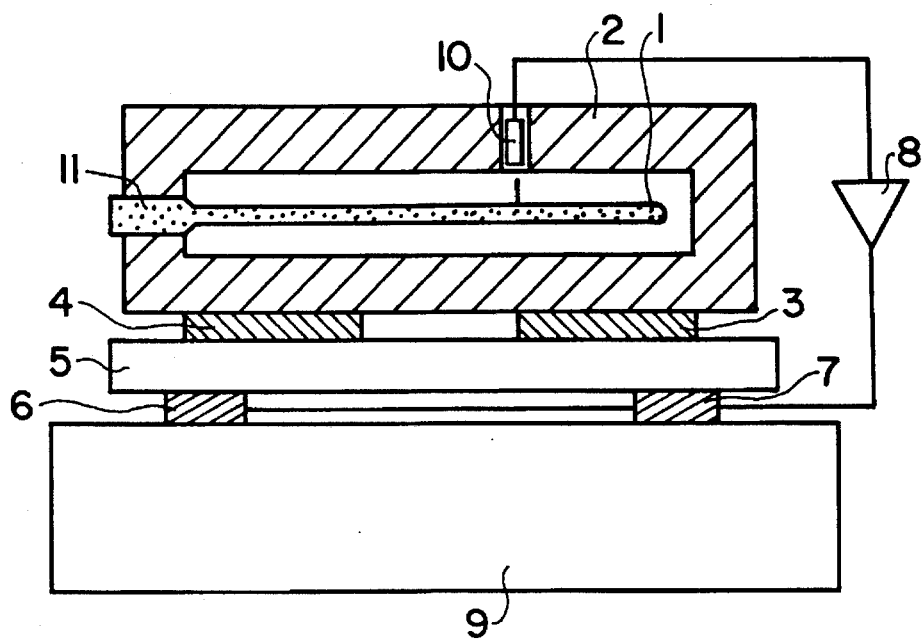
FIG. 1 shows a schematic view of a first embodiment of the invention in which the oscillator is disposed within a housing.

The apparatus has an oscillator 1 which is preferably embodied in the shape of a letter U and in which the sample to be tested is contained. In a first embodiment of the invention, oscillator 1 is attached to a support included in a housing 2 at installation site 11.

The housing 2 of the oscillator 1 is disposed, via thermostatically-controllable elements in the form of Peltier elements 3, 4, on a thermostatically-controllable plate 5, for example, a cooling plate. The latter is disposed, in turn, on the actuators 6, 7, and these are disposed on a countermass 9.

The drive of the actuators 6, 7, formed by piezo-electric elements, takes place by means of an oscillation amplifier 8 which in turn is controlled by a sensor 10 disposed in the housing 2 of the oscillator 1.

The density measurement is based on the oscillation method. The latter is based on the determination of the period τ of an oscillating body which is shaped such that a defined volume, formed by the interior of the oscillator 1, of the test sample to be tested takes part in the oscillation and in this way affects the period length τ. For the purpose of calculation, the period length τ of an oscillator used for measuring density is replaced by a simple mass-spring model:

$$\tau = 2\pi \sqrt{\frac{M_o + \rho V}{c}}$$

where $M_o$ is the mass of the empty oscillator, c its resilient constant and the product $\rho V$ is the test sample mass participating in the oscillation and resulting from the test sample volume V and the density of the test sample. The quotients $M_o/c$ and $V/c$ can be considered to be oscillator-specific apparatus constants and can be calculated from the determination of the oscillation length of the oscillator filled with two calibration test samples.

Following transformation and definition of more practical constants A and $T_o$, the following results:

$$\rho = \frac{1}{A} \times (T^2 - T_o^2)$$

where T is a whole number multiple of the period length τ, $T_o$ is a multiple of the period length $\tau_o$ of the empty oscillator, increased by the same factor. The factors A and $T_o$ are calculated by setting the last equation for two value pairs ρ, T and solving in accordance with the factors A and $T_o$.

The energy required for maintaining the oscillations is supplied to the oscillator 1 via the oscillation amplifier 8 and the actuators 6, 7 connected to it.

It is particularly stressed that the invention is not limited to the thermostatically-controllable plate described in connection with the above exemplary embodiment, nor to the Peltier elements. These steps are used to improve the desired increased reduction of the temperature effects, which can already be attained to a very satisfactory extent in that the actuators 6, 7 are directly disposed on the countermass 9, for example.

In this case it is possible in accordance with the invention to attain an improvement of the thermal insulation in that in the above embodiment the thermostatically-controllable elements 3 or 4, for example Peltier elements, are directly disposed between the individual actuators 6 or 7 and the oscillator 1 or its housing, i.e., that the thermostatically-controllable plate is omitted.

Figure 2:
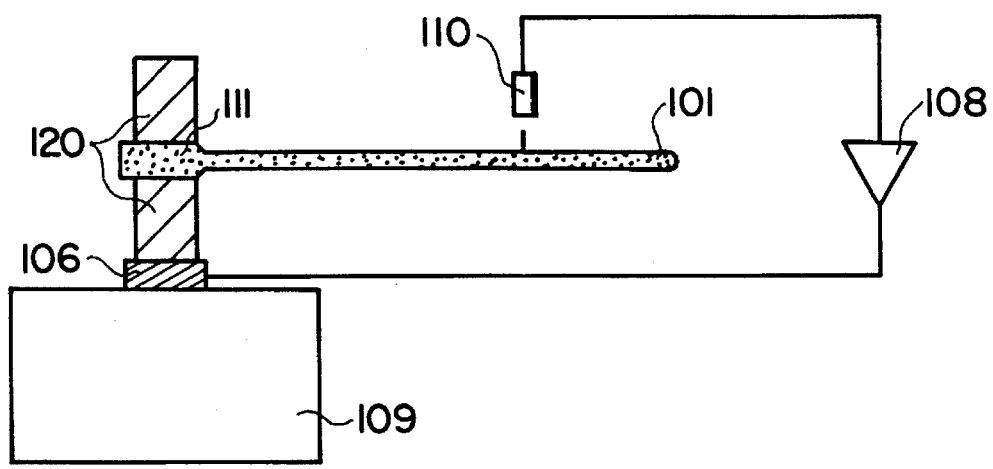
FIG. 2 shows a schematic view of a second embodiment of the invention in which the oscillator is not disposed within a housing but is disposed directly on one or more actuators.

A second embodiment of the invention is depicted in FIG. 2. In this embodiment, the oscillator housing is eliminated and actuator 106 is directly interposed between installation site 111 and countermass 109. Though not shown in the figure, a thermostatically-controllable plate may be used in a manner similar to that of the first embodiment. Also, thermostatically-controllable elements may be included as in the first embodiment.

FIG. 2 also shows sensor 110, oscillator 101 and oscillator amplifier 108, those items being respectively connected in a manner similar to items 10, 1 and 8 of FIG. 1. Additionally, FIG. 2 shows a support 120 attached to the oscillator, separating the oscillator from the actuator.

What is claimed is:

1. An apparatus for determining liquid and gas density, said apparatus comprising:

an oscillator filled with a test sample;

at least one actuator coupled to said oscillator, said actuator being responsive to an electric signal;

means for thermal insulation disposed between said actuator and said oscillator; and an oscillation amplifier for producing said electric signal.

2. The apparatus of claim 1, said means for thermal insulation comprising a thermostatically-controllable plate.

3. The apparatus of claim 2, further comprising:

at least one thermostatically-controllable element for supporting at least one of said oscillator and said oscillator housing on said thermostatically-controllable plate.

4. The apparatus of claim 3, said at least one thermostatically-controllable element comprising a Peltier element.

5. The apparatus of claim 1, said means for thermal insulation comprising at least one thermostatically-controllable element;

wherein said at least one thermostatically-controllable element is disposed between said at least one actuator and at least one of said oscillator and said oscillator housing.

6. The apparatus of claim 5, said at least one thermostatically-controllable element comprising a Peltier element.

7. An apparatus for determining liquid and gas density, said apparatus comprising:

a support;

an oscillator filled with a test sample attached to said support;

at least one actuator for moving said oscillator and said support in response to an electric signal;

an oscillation amplifier for generating said electric signal; and a countermass upon which said at least one actuator is disposed, said support moving relative to said countermass.

8. An apparatus for determining liquid and gas density, said apparatus comprising:

an oscillator filled with a test sample;

a support attached to said oscillator;

at least one actuator responsive to an electric signal and connected to said support, said actuator being separated from said oscillator by said support; and an oscillation amplifier for producing said electric signal.

9. The apparatus of claim 8 further comprising a countermass attached to said actuator, said countermass reducing temperature fluctuations in said actuator.

10. The apparatus of claim 9, wherein said actuator is positioned between said countermass and said support.

11. The apparatus of claim 8 further comprising a housing surrounding said oscillator.

\* \* \* \* \*